United States Patent [19]

Bucalo

[11] 3,951,132
[45] Apr. 20, 1976

[54] IMPLANT AND IMPLANTING METHOD
[75] Inventor: Louis Bucalo, Holbrook, N.Y.
[73] Assignee: Investors in Ventures, Inc., New York, N.Y.
[22] Filed: Apr. 15, 1974
[21] Appl. No.: 461,009

Related U.S. Application Data
[63] Continuation-in-part of Ser. No. 359,429, May 11, 1973, Pat. No. 3,815,578.

[52] U.S. Cl. ............................. 128/1 R; 128/334 R
[51] Int. Cl.² ........................................ A61B 19/00
[58] Field of Search ............. 128/1 R, 334 R, 334 C; 3/1

[56] References Cited
UNITED STATES PATENTS

| | | | |
|---|---|---|---|
| 2,453,056 | 11/1948 | Zack | 128/334 |
| 3,123,077 | 3/1964 | Alcamo | 128/335.5 |
| 3,221,746 | 12/1965 | Noble | 128/334 R |
| 3,308,819 | 3/1967 | Arp | 128/215 |
| 3,646,615 | 3/1972 | Ness | 3/1 |
| 3,699,957 | 10/1972 | Robinson | 128/1 R |

Primary Examiner—Dalton L. Truluck
Attorney, Agent, or Firm—Steinberg and Blake

[57] ABSTRACT

An implant which includes an elongated member to be situated in the interior of a tubular body organ and carrying at its exterior a structure for promoting the ingrowth of tissue, this structure being situated inwardly from a free end of the elongated member which enters the tubular organ in advance of the ingrowth structure. Between this free end of the elongated member and the ingrowth structure are barbs which are fixed to the elongated member, which are circumferentially distributed about the latter, and which are inclined away from the free end of the elongated member and extend over the ingrowth structure. These barbs are flexible so that they are capable of being radially deflected toward the elongated member. When the elongated member is to be introduced into the tubular organ, the latter is gripped with tweezers which have teeth which engage the tubular organ and which are circumferentially distributed about the latter. The tweezer teeth are out of longitudinal alignment with the barbs so that when the teeth and barbs pass each other during introduction of the implant into the tubular organ, while the latter is pulled onto the elongated member with the tweezers, the tweezer teeth will be aligned with spaces between the barbs.

10 Claims, 11 Drawing Figures

IMPLANT AND IMPLANTING METHOD

CROSS REFERENCE TO RELATED APPLICATION

This application is a continuation-in-part of copending Pat. application Ser. No. 359,429, filed May 11, 1973 and entitled Method of Inserting an Implant into a Portion of a Tubular Organ Whose Mucous Lining has been Partially Removed now U.S. Pat. No. 3,815,578.

BACKGROUND OF THE INVENTION

The present invention relates to implants.

In particular, the present invention relates to implants which have an elongated configuration and which are intended to be introduced into a tubular body organ.

As is well known, when an implant of this type is introduced into a tubular body organ, it is important to fix the implant in the tubular body organ. For this purpose such implants have been provided at their exterior with a tissue-ingrowth structure in the form of a porous matrix having pores into which the tissue will grow in order to provide a secure positioning of the implant in the body organ. In addition, this secure positioning is of particular importance in connection with implants such as vas valves which are received in a vas deferens because the engagement of the exterior of the valve with the tissue of the vas deferens will reliably prevent sperm from travelling along the exterior of the valve, thus bypassing the latter and defeating the purpose of the valve. Thus in general it is important to fixedly determine the location of the implant in the tubular organ and in certain specific cases such as the case of the vas valve, other important objectives are to be achieved by the growth of tissue into the pores of the ingrowth structure.

During the time interval immediately subsequent to introduction of the implant, the tissue has not yet grown into the ingrowth structure, so that it becomes necessary to provide the best possible conditions for tissue ingrowth while maintaining the implant in the desired position through means other than the ingrowth of tissue. For the purpose it has been customary to use sutures, but the application of sutures by a surgeon has proved to be extremely inconvenient and furthermore does not achieve the desired results in the best possible manner. Thus, even if sutures are used for temporarily holding the implant in position in the interior of the tubular body organ, it is still possible for the tubular body organ to move with respect to the implant. Thus even if sutures are capable of preventing, at least to some extent, longitudinal movement of the tubular body organ and the implant one with respect to the other, such sutures cannot prevent circumferential or twisting movement of the tubular body organ and the implant one with respect to the other. Any movment of this type, whether longitudinal or circumferential twisting, between the implant and the tubular body organ, retards the growth of tissue since the tissue will grow into the ingrowth structure in an ideal manner only when the tissue which engages the ingrowth structure is immobilized with respect thereto.

SUMMARY OF THE INVENTION

It is accordingly a primary object of the present invention to provide an implanting method, as well as an implant and an implanting tool, all of which will contribute to achievement of the result of immobilizing the tissue with respect to the implant so that when the implant has an ingrowth structure the tissue will grow as rapidly as possible into the ingrowth structure.

In addition, however, it is an object of the present invention to provide an implant as well as an implanting method and tool which will prevent undesirable injury to the tubular organ either by the implant or by manipulations in connection with the implanting method.

Thus, it is an object of the present invention to provide an implant which on the one hand will not injure the tubular organ when the implant is introduced into the tubular organ and which on the other hand when it is introduced is capable of achieving a perfect immobilization of the inner surface of the tubular organ with respect to at least part of the implant where an ingrowth structure is located.

In addition, it is an object of the present invention to provide a method for introducing the implant in such a way that the introduction of the implant can be carried out in a highly effective and convenient, rapid manner, even by a relatively unskilled surgeon.

In addition it is an object of the present invention to provide a tool by means of which it is possible to manipulate the tubular organ during introduction of the implant into the latter.

Furthermore it is an object of the present invention to provide a tool of this type which is designed in such a way that there will be no interference between the tool and parts of the implant.

The implant of the invention includes an elongated member having a free end which is first introduced into a tubular organ in advance of the remainder of the elongated member, the latter carrying a tissue-ingrowth means spaced inwardly from the free end as well as a flexible barb means situated between the free end of the elongated member and the tissue-ingrowth means carried thereby. The barb means includes flexible barbs which are inclined away from the free end of the elongated member and which are capable of radially deflecting inwardly toward the elongated member. Thus when the implant is introduced these barbs can be deflected inwardly toward the elongated member so as to provide substantially no resistance to introduction of the implant while at the same time preventing any injury to the tubular organ. At the same time the pointed ends of the barbs will act to prevent retraction of the tubular organ from the implant while at the same time maintaining the inner surface of the tubular organ which engages the ingrowth means immobilized with respect to the latter so that there can be no longitudinal or circumferential twisting movement between the ingrowth means and the tissue which is to grow into the latter.

During introduction of this implant, in accordance with the method of the invention, the tubular organ is gripped by tweezers which greatly facilitate pulling of the tubular organ onto the elongated member while the latter is introduced into the tubular organ. The barbs carried by the elongated member are circumferentially distributed about the latter and the tweezers have teeth which are circumferentially distributed about the tubular organ but are angularly out of alignment with the barbs so that while the barbs and the tweezer teeth pass each other during introduction of the implant into the tubular organ, the tweezer teeth will be aligned with spaces between the barbs so that the teeth of the tweezers do not exert any undesirable pressure on the barbs.

BRIEF DESCRIPTION OF DRAWINGS

The present invention is illustrated by way of example in the accompanying drawings which form part of this application and in which.

DESCRIPTION OF PREFERRED EMBODIMENTS

Figure 1:
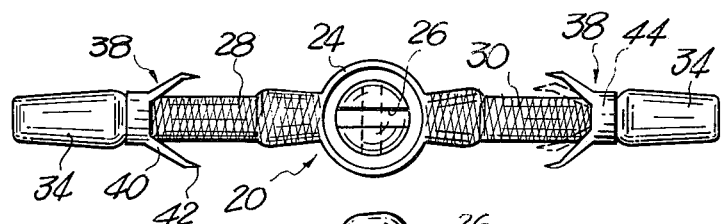
FIG. 1 is a partly schematic top plan view of one embodiment of an implant according to the invention.
Figure 2:
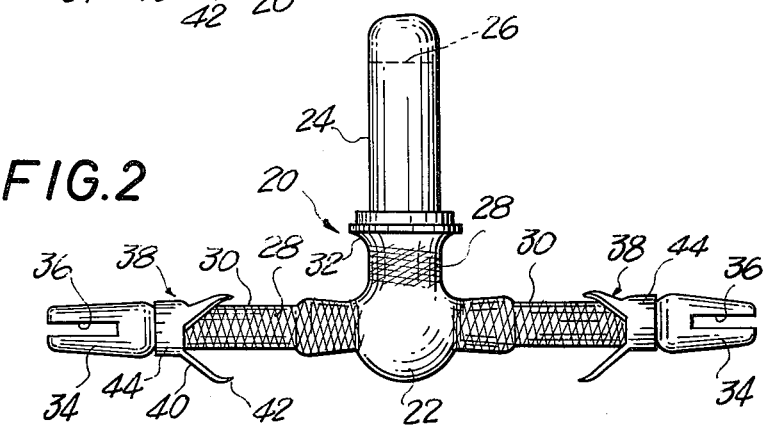
FIG. 2 is an elevation of the structure of FIG. 1.

Referring first to FIGS. 1 and 2, there is illustrated therein one possible embodiment of an implant according to the present invention. The illustrated implant is a vas valve adapted to be implanted in a vas deferens for reversibly interrupting the flow of sperm-carrying fluid. The illustrated valve implant 20 includes a central portion 22. This portion 22 is in the form of a valve housing in which a rotary valve member is located, this rotary valve member being connected to the stem 24 which is adapted to project from the vas deferens after the implant has been introduced therein. The stem 24 is formed at its top end with a slot 26, the valve being open when the slot 26 is in the solid line position of FIG. 1 and being closed when the slot 26 is in the dotted line position of FIG. 1.

The implant 20 carries at its exterior a tissue-ingrowth means for promoting the ingrowth of tissue from the inner surface at the lumen of the tubular organ into pores defined by the tissue-ingrowth means. Such a tissue-ingrowth means may take the form of a suitable matrix formed with pores into which the tissue will grow. In the specific example illustrated extremely fine gold wire 28 is wound in a number of layers around the elongated portions 30 of the implant, these elongated portions 30 extending symmetrically in opposite directions from the central portion 22 and having a common axis. The tissue-ingrowth means 28 is located not only along the elongated portions 30 of the implant but also around the neck 32 of the central portion 22 of the implant. Thus, the fine gold wire which is wound in several layers to form the tissue-ingrowth means 28 will form between the wire convolutions interstices which define fine pores into which the tissue will grow. However it is to be understood that another ingrowth structure such as a suitably porous deposit may be located at the exterior of the implants to form the tissue-ingrowth means.

Each of the elongated portions 30 of the illustrated implant 20 terminates in a free end 34 which is suitably tapered as illustrated to facilitate introduction of each free end 34 into the tubular organ in advance of the remainder of the elongated portion 30. These free ends 34 are formed with inwardly extending slots 36 which act to prevent plugging of the tubular passage extending along the interior of each of the elongated portions 30.

In accordance with a particular feature of the present invention, a flexible barb means 38 is carried by each elongated member 30 between the free end 34 thereof and the tissue-ingrowth means 28. In the illustrated example each of the flexible barb means 38 includes three flexible barbs 40 uniformly distributed circumferentially arorund each elongated member 30 so that the barbs 40 of each elongated member are angularly spaced from each other by 120°. Each of these flexible barbs 40 terminates in a pointed free end 42. The barbs 40 extend from a circular portion 44 of each barb means. This circular portion 44 forms a fixing means for fixing the flexible barbs 40 to the elongated member 30 and may be swaged onto each tubular member 30 or may be bonded thereto either by way of a suitable cement or by utilizing some of the convolutions of the wire of the tissue-ingrowth means for fixing the barb means 38 to each elongated member 30.

The flexible barb means 38 may be made of a suitable material. For example stainless steel may be used for this purpose, although it is possible also to use a suitable plastic which will be inert with respect to the body. In addition it is possible to use for this purpose well known materials which become absorbed into the body after passage of a given time.

Because the barbs 40 are capable of readily being deflected inwardly toward the elongated member 30 which carries the barbs, as shown in dot-dash lines at the right of FIG. 1, these barbs will be easily deflected by the inner surface of the tubular organ as it is advanced over the elongated member 30 to receive the latter, and thus the barbs will not injure the tubular organ and will provide no substantial resistance to introduction of the implant into the tubular organ. On the other hand the barbs, as a result of their inherent resiliencey, tend to expand outwardly and thus the pointed ends 42 of the barbs will be received in the tissue of the tubular organ to prevent any longitudinal retraction of the tubular organ from the implant.

At the same time, these barbs act in a most effective manner to prevent any turning or twisting of the tubular organ with respect to the implant at the portion where the ingrowth means 28 is located. Thus a complete immobilization of the tubular organ at its inner surface which engages the ingrowth means 28 is achieved, and this factor is of exceedingly great importance because such an immobilization provides for an undisturbed and therefore extremely rapid growth of the tissue into the ingrowth means.

It is apparent, therefore, that with the structure of the invention on the one hand sutures are not required because the barbs will themselves act to maintain the implant in the tubular organ while on the other hand a perfect immobilization of the tubular organ with respect to the ingrowth means is achieved inasmuch as the barbs are situated outboard of the ingrowth means. Thus that part of the tubular organ which is situated inwardly of the barbs between the latter and the central region 22 of the implant engages the ingrowth means and is immobilized to promote the ingrowth of tissue in the best possible manner.

According to a further important feature of the present invention, a tool means is provided for facilitating the introduction of the implant into the tubular organ, and this tool means as well as the manner in which it is used are illustrated in FIGS. 3–11.

Figure 3:
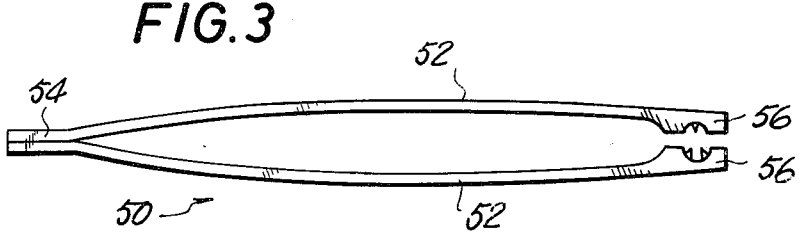
FIG. 3 is a side elevation of tweezers of the invention.

Thus, in the example of FIG. 3 the illustrated tool means 50 takes the form of a tweezers having a pair of springy flexible arms 52 joined in a well known manner to each other at their left ends 54, as viewed in FIG. 3.

Figure 4:
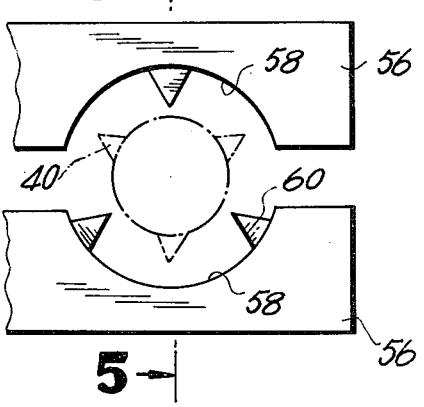
FIG. 4 is an enlarged view of the right end of the structure of FIG. 3.
Figure 5:
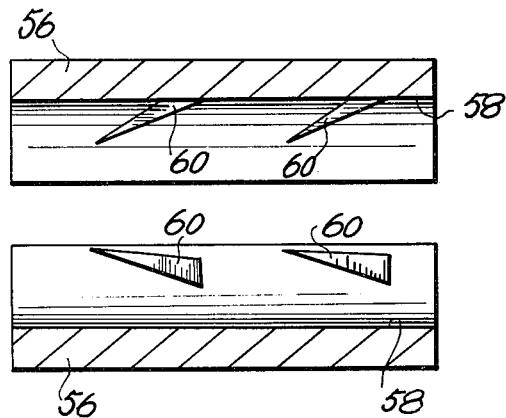
FIG. 5 is a transverse section of the structure of FIG. 4 taken along line 5—5 of FIG. 4 in the direction of the arrows.

As is shown at an enlarged scale in FIG. 4, each of the arms 52 terminates in a free end region 56 formed with a groove 58, and the pair of grooves 58 substantially form parts of a cylinder whose axis extends transversely across the arms 52. Thus the tubular organ is capable of being received in the groove 58 to be gripped between the free end portions 56 of the arms 52.

In accordance with a further feature of the invention, the free end portions 56 are provided with teeth 60 situated in the grooves 58. In the example illustrated in FIGS. 4 and 5 the illustrated upper free end portion 56 carries a pair of axially aligned teeth 60 while the lower free end portion 56 carries two pairs of teeth 60 with the teeth in each pair being axially aligned as illustrated. Moreover it will be noted from FIG. 5 that all of the teeth 60 are inclined in the same direction toward the left side edge of the pair of arms 52 of the tweezers 50. Thus the tool is used in such a way that the teeth 60 are inclined in the direction in which the tubular organ is moved onto the implant so that the teeth 60 will become inserted into the tissue of the tubular organ and facilitate the movement of the tubular organ onto the implant while the latter is received in the tubular organ.

Furthermore, in accordance with a further feature of the present invention where each barb means has the construction described above in connection with FIGS. 1 and 2 according to which each barb means includes three barbs uniformly distributed circumferentially about the member 30, there are three sets of teeth 60 also uniformly distributed circumferentially about the axis which extends across the tweezer arms and which forms the central axis of a cylinder of which the surfaces of the grooves 58 form a part, at least substantially. With this arrangement the teeth of the tweezers are situated so as to be "out-of-phase" with respect to the barbs, as indicated in dot-dash lines in FIG. 4. As a result of this feature the teeth of the tool become aligned with the spaces between the barbs when the barbs and the teeth 60 move past each other.

Figure 6:
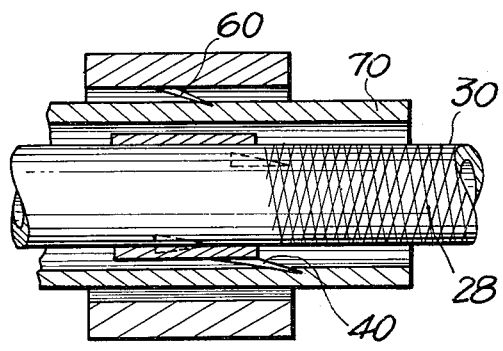
FIG. 6 is a schematic elevation of the method of the invention.
Figure 7:
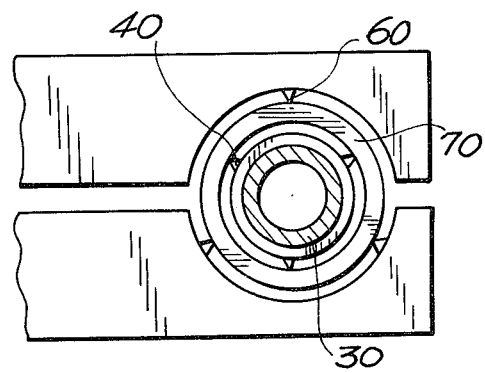
FIG. 7 is a transverse view of the method illustrated in FIG. 6.

This latter feature of the method of the present invention is shown most clearly in FIGS. 6 and 7. As may be seen from FIGS. 6 and 7, the teeth 60 are inclined toward the right so as to pull the tubular organ 70 toward the right onto the portion 30 of the implant which advances toward the left into the tubular organ. The barbs 40 are also inclined toward the right so that they will be readily deflected by the inner surface of the tubular organ 70. On the other hand, as is apparent both from FIGS. 6 and 7, as well as FIG. 4, as the teeth 60 and the barbs 40 move past each other, the teeth 60 are aligned with spaces between the barbs 40 and the barbs 40 are aligned with spaces between the teeth 60, so that the teeth 60 will not have any tendency to push the barbs inwardly against the implant. Thus undesired pressure on the barbs is avoided in this way and undesired resistance to introduction of the implant into the tubular organ is also avoided.

Figure 8:
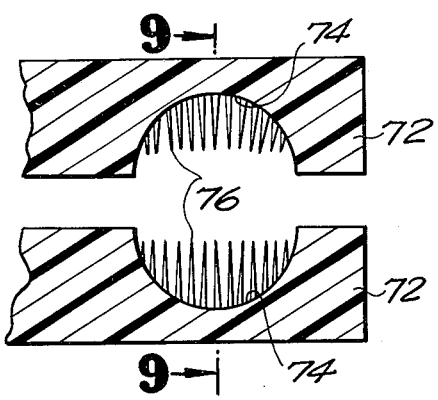
FIG. 8 is a fragmentary side elevation of another embodiment of tweezers of the invention.
Figure 9:
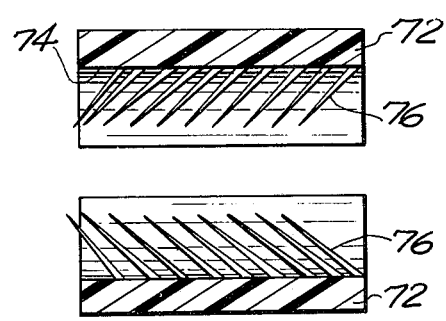
FIG. 9 is a transverse section of the structure of FIG. 8 taken along line 9—9 of FIG. 8 in the direction of the arrows.

The tool 50 may be made of any suitable metal or molded plastic. A further embodiment which may be made of a molded plastic is shown in FIGS. 8 and 9. As may be seen from FIGS. 8 and 9, the free end regions 72 of a pair of tweezer arms which may be made of plastic are also formed with grooves 74 which may be identical with the grooves 58. However in this case the molded plastic 72 has integrally molded therewith a relatively large number or teeth 76 in the form of bristles similar to toothbrush bristles, for example. As may be seen from FIG. 9, the birstles 76 are all inclined in the same direction toward one of the side edges of each of the arms of the tweezers. Because of the relative softness of the bristles, they are readily displaced by the barbs while passing thereover, while at the same time those bristles or teeth 76 which are out of alignment with the barbs will not have any tendency to be deflected by the barbs. Because of the ease with which the bristles or teeth 76 can be flexed, they will not push the barbs undesirably inwardly toward the implant and in particular against the tissue ingrowth means. At the same time because of the relatively large number of these teeth or bristles 76, they will engage the tublar organ at its exterior at a large number of locations providing an exceedingly effective holding of the tubular organ while the latter is advanced onto the implant.

Figure 10:
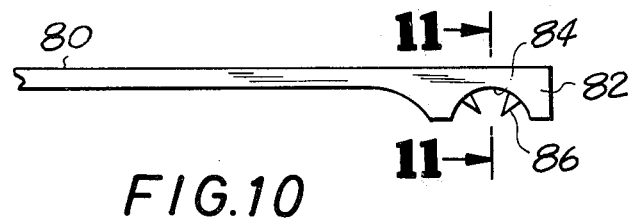
FIG. 10 is a fragmentary elevation of another embodiment of a tool adapted to be used according to the present invention.
Figure 11:
FIG. 11 is a transverse section of part of the tool of FIG. 10 taken along line 11—11 of FIG. 10 in the direction of the arrows.

A further embodiment of a suitable tool according to the invention is shown in FIGS. 10 and 11. According to this embodiment the tool includes a single arm 80 forming in effect one half of a tweezers. This single arm 80 terminates in a free end region 82 formed with a groove 84 which may correspond to the groove 58. Situated in the groove 84 are two pairs of teeth 86, with the teeth of each pair being axially aligned as illustrated in FIG. 11. Moreover these teeth also are inclined toward one side edge of the arm 80. Thus, with this construction even though the tubular organ is not gripped between a pair of arms, nevertheless it is possible to introduce the teeth 86 at their pointed ends into the tissue at the exterior of the tubular organ and effecitvely pull on the tubular organ while it is advanced over the implant, so that it is also possible to use a tool as shown in FIGS. 10 and 11 for the purposes of the present invention.

Of course, the pairs of teeth 86 are positioned so as to be angularly out of alignment with the barbs.

It is to be noted in this latter connection that when an implant as shown in FIGS. 1 and 2 is introduced, the orientation of the barbs is noted by the surgeon. Thus it is known that spaces between a pair of barbs are in axial alignment with the stem 24 or the neck 32 of the central housing 22. Therefore, the surgeon is capable of readily aligning the teeth of the tweezers or tool 80 with spaces between the barbs simply by locating one set of teeth in a plane which contains the axis of the stem 24.

It is apparent, therefore, that with the implant, implanting method, and tool of the present invention it becomes possible in a highly effective manner to introduce an implant rapidly while achieving for the implant a secure positioning in the tubular organ even though sutures are not used. Thus the barbs serve not only to secure the implant in the tubular organ but also they effectively prevent any relative movement between the tissue at the lumen and the ingrowth means engaged by the tissue so that an undistrubed growth of tissue into the ingrowth means is assured.

What is claimed is:

1. In a method for introducing an implant into the interior of a tubular body organ, the steps of connecting to the implant inwardly of a free end thereof which is to be introduced first into the tubular organ in advance of the remainder of the implant a plurality of flexible barbs circumferentially distributed about the implant and inclined inwardly away from the free end thereof while being capable of flexing substantially radially toward and away from the part of the implant which carries the barbs, and then introducing the implant into the interior of a tubular organ with the free end of the implant entering first in advance of the barbs while simultaneously placing in engagement with the tubular organ at the exterior thereof a tool which is capable of being manipulated for pulling the tubular organ over the implant to an extent sufficient to situate an interior surface of the tubular organ inwardly beyond the barbs while deflecting the latter radially toward the part of the implant which carries the barbs, so that the barbs will oppose longitudinal retraction of the tubular organ from the implant without injuring the tubular organ during introduction of the implant, said tool having teeth which are inserted into the tubular organ at the exterior thereof, and situating said teeth out of circumferential alignment with barbs so that when the barbs and teeth move past each other, the teeth of the tool will be aligned with the spaces between the barbs.

2. In a method for introducing an implant into the interior of a tubular body organ, the steps of connecting to the implant inwardly of a free end thereof which is to be introduced first into the tubular organ in advance of the remainder of the implant a plurality of flexible barbs circumferentially distributed about the implant and inclined inwardly away from the free end thereof while being capable of flexing substantially radially toward and away from the part of the implant which carries the barbs, and then introducing the implant into the interior of a tubular organ with the free end of the implant entering first in advance of the barbs while simultaneously placing in engagement with the tubular organ at the exterior thereof a tool which is capable of being mainpulated for pulling the tubular organ over the implant to an extent sufficient to situate an interior surface of the tubular organ inwardly beyond the barbs while deflecting the latter radially toward the part of the implant which carries the barbs, so that the barbs will oppose longitudinal retraction of the tubular organ from the implant without injuring the tubular organ during introduction of the implant, situating on the implant inwardly of and adjacent the barbs a tissue-ingrowth means into which tissue of the tubular organ will grow from the inner surface of the tubular organ, so that said barbs act to immobilize the part of the tubular organ which engages the tissue ingrowth means to promote an undisturbed growth of tissue into the ingrowth mean, said tool being in the form of tweezers having teeth which are inserted into the tubular organ, said tweezer teeth being circumferentially distributed about the tubular organ, and angularly situating the latter teeth in longitudinal alignment with spaces between the barbs so that as the tweezer teeth and barbs move past each other the tweezer teeth will be circumferentially aligned with spaces between the barbs.

3. In a method as recited in claim 2 and wherein the tubular organ is a vas deferens and the implant is a valve.

4. In a method as recited in claim 3 and wherein the valve has a central portion and a pair of elongated tubular portions extending coaxially in opposite directions from the central portion, and carrying out said steps on both of the elongated portions of the valve.

5. In an implant which is to be situated in a tubular body organ, an elongated member having a free end which is to be introduced first into the tubular body organ in advance of the part of said elongated member which extends from said free end thereof, flexible barb means, and fixing means connected to said flexible barb means and carried by said member inwardly of said free end thereof for fixing said flexible barb means thereto in a position inclined inwardly away from said free end to be deflected substantially radially toward said elongated member by an inner surface of the tubular organ, whereby said flexible barb means provides substantially no resistance to introduction of the implant into the tubular organ while automatically opposing retraction of the tubular organ from the implant, and tissue-ingrowth means carried by said elongated member adjacent said flexible barb means at the side thereof opposite from said free end so that said flexible barb means act to immobilize an inner surface of the tubular organ with respect to said tissue-ingrowth means.

6. The combination of claim 5 and wherein said barb means includes barbs made of metal.

7. The combination of claim 5 and wherein said barb means includes barbs made of plastic.

8. The combination of claim 5 and wherein said barb means includes barbs made of a material capable of being absorbed by the body.

9. In an implant which is to be situated in a tubular body organ, an elongated member having a free end which is to be introduced first into the tubular body organ in advance of the part of said elongated member which extends from said free end thereof, flexible barb means, and fixing means connected to said flexible barb means and carried by said member inwardly of said free end thereof for fixing said flexible barb means thereto in a position inclined inwardly away from said free end to be deflected substantially radially toward said elongated member by an inner surface of the tubular organ, whereby said flexible barb means provides substantially no reistance to introduction of the implant into the tubular organ while automatically opposing retraction of the tubular organ from the implant, said elongated member forming part of a valve to be introduced into a vas deferens, said valve having a central portion on one side of which said elongated member is located and including a second elongated member situated on the opposite side of said central portion from said first-mentioned elongated member and being symmetrical therewith, both of said elongated members having diameters small enough to be situated in the lumen of a vas deferens and said elongated members respectively carrying said fixing means connected to said flexible barb means, and both of said flexible barb means being inclined inwardly away from the free ends of said elongated members toward said central portiton of said valve for yielding radially inwardly toward said elongated members when the latter are introduced into the lumen of a vas deferens while tending to dig into the inner surface of the vas deferens in response to any tendency for the elongated members to be removed from the vas deferens so that said flexible barb means hold said elongated members reliably in the lumen of a vas deferens.

10. In an implant which is to be situated in a tubular body organ, an elongated member having a free end which is to be introduced first into the tubular body organ in advance of the part of said elongated member which extends from said free end thereof, flexible barb means, and fixing means connected to said flexible barb means and carried by said member inwardly of said free end thereof for fixing said flexible barb means thereto in a position inclined inwardly away from said free end to be deflected substantially radially toward said elongated member by an inner surface of the tubular organ, whereby said flexible barb means provides substantially no resistance to introduction of the implant into the tubular organ while automatically opposing retraction of the tubular organ from the implant, said elongated member forming part of a valve to be introduced into a vas deferens, said valve having a central portion on one side of which said elongated member is located and including a second elongated member situated on the opposite side of said central portion from said first-mentioned elongated member and being symmetrical therewith, both of said elongated members respectively carrying said fixing means connected to said flexible barb means, and both of said flexible barb means being inclined inwardly away from the free ends of said elongated members toward said central portion of said valve, said elongated members carrying a tissue-ingrowth means between and adjacent said flexible barb means.

* * * * *